(12) United States Patent
Luo et al.

(10) Patent No.: US 12,390,193 B2
(45) Date of Patent: Aug. 19, 2025

(54) DETECTION PROBE, TRANSMISSION DEVICE, AND DETECTION INSTRUMENT

(71) Applicant: EDAN INSTRUMENTS, INC., Shenzhen (CN)

(72) Inventors: Hua Luo, Shenzhen (CN); Dan Zhou, Shenzhen (CN); Qi Ma, Shenzhen (CN); Bo Ouyang, Shenzhen (CN); Jianhua Mo, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 109 days.

(21) Appl. No.: 18/472,263

(22) Filed: Sep. 22, 2023

(65) Prior Publication Data

US 2024/0008848 A1   Jan. 11, 2024

Related U.S. Application Data

(63) Continuation of application No. PCT/CN2021/082438, filed on Mar. 23, 2021.

(51) Int. Cl.
*A61B 8/00* (2006.01)

(52) U.S. Cl.
CPC .......... *A61B 8/4494* (2013.01); *A61B 8/4444* (2013.01)

(58) Field of Classification Search
None
See application file for complete search history.

(56) References Cited

U.S. PATENT DOCUMENTS

| | | |
|---|---|---|
| 2006/0173330 A1 | 8/2006 | Kim |
| 2008/0015444 A1 | 1/2008 | Cho |
| 2011/0071398 A1 | 3/2011 | Hwang et al. |
| 2016/0113623 A1* | 4/2016 | Tang ................... G01S 7/52079 600/459 |

FOREIGN PATENT DOCUMENTS

| | | |
|---|---|---|
| CN | 102018531 A | 4/2011 |
| CN | 201949038 U | 8/2011 |
| CN | 102783974 A | 11/2012 |

(Continued)

OTHER PUBLICATIONS

English translation for CN 201949038.*

(Continued)

*Primary Examiner* — Shahdeep Mohammed

(57) ABSTRACT

A detection probe, a transmission device, and a detection instrument. The detection probe includes a housing defining a receiving space, a detection mechanism disposed on an end of the housing and configured to perform a detection function, a drive mechanism disposed in the receiving space and configured to output power, a rope transmission mechanism disposed in the receiving space and including a rope connected to the driving mechanism and the detection mechanism respectively and a reversing assembly including at least two reversing pulley groups arranged along an extension path of the rope, and a gear transmission mechanism disposed in the receiving space and connected to the driving mechanism and the rope transmission mechanism respectively, so as to receive the power output by the driving mechanism and transmit the power to the rope transmission mechanism.

20 Claims, 9 Drawing Sheets

(56) References Cited

FOREIGN PATENT DOCUMENTS

| | | | |
|---|---|---|---|
| CN | 103356240 | A | 10/2013 |
| CN | 104224228 | A | 12/2014 |
| CN | 105662467 | A | 6/2016 |
| CN | 208388639 | U | 1/2019 |

OTHER PUBLICATIONS

English translation for CN 208388639.*
International search report and Written Opinion of the International Search Authority,International Application No. PCT/CN2021/082438,mailed Dec. 22, 2021 (17 pages).
European Search Report,European Application No. 21932080.1, mailed Mar. 7, 2024 (7 pages).

* cited by examiner

DETECTION PROBE, TRANSMISSION DEVICE, AND DETECTION INSTRUMENT

CROSS REFERENCE TO RELATED APPLICATIONS

The present disclosure is a continuation of International Patent Application No. PCT/CN2021/082438, filed Mar. 23, 2021, the contents of which are herein incorporated by reference in their entireties.

TECHNICAL FIELD

The present disclosure relates to the field of medical instruments, in particular to a detection probe, a transmission device, and a detection instrument.

BACKGROUND

A detection probe used for medical detecting, such as an ultrasonic probe, may emit ultrasonic signal for detection through an acoustic head assembly and receive an ultrasonic signal including detection information, and a detection result is obtained through analysis.

In practical applications, in order to improve accuracy and comprehensiveness of the detection result, the acoustic head assembly may be driven to oscillate to detect different parts. However, due to factors such as structural and spatial limitations, etc., the requirement for a transmission mechanism configured to transmit driving force to the acoustic head assembly becomes higher and higher.

SUMMARY OF THE DISCLOSURE

According to a first aspect of the embodiments of the present disclosure, a detection probe is provided. The detection probe includes: a housing, defining a receiving space; a detection mechanism, disposed on an end of the housing and configured to perform a detection function; a driving mechanism, disposed in the receiving space and configured to output power; a rope transmission mechanism, disposed in the receiving space and including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups; and a gear transmission mechanism, disposed in the receiving space and connected to the driving mechanism and the rope transmission mechanism respectively, so as to receive the power output by the driving mechanism and transmit the power to the rope transmission mechanism.

According to a second aspect of the embodiments of the present disclosure, a transmission device is provided and applied to a detection probe. The detection probe includes a detection mechanism and a driving mechanism. The transmission device includes: a rope transmission mechanism, including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups.

According to a third aspect of the embodiments of the present disclosure, a detection instrument is provided. The detection instrument includes a host and a detection probe. The detection probe includes: a housing, defining a receiving space; a detection mechanism, disposed on an end of the housing and configured to perform a detection function; a driving mechanism, disposed in the receiving space and configured to output power; a rope transmission mechanism, disposed in the receiving space and including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups; and a gear transmission mechanism, disposed in the receiving space and connected to the driving mechanism and the rope transmission mechanism respectively, so as to receive the power output by the driving mechanism and transmit the power to the rope transmission mechanism. The host is respectively connected to the detection mechanism and the driving mechanism of the detection probe, such that the driving mechanism is controlled to output the power, and the detection mechanism is controlled to perform the detection function.

BRIEF DESCRIPTION OF THE DRAWINGS

To illustrate technical solutions more clearly in the embodiments of the present disclosure or in the related art, the drawings used for description of some embodiments or the related art will be briefly described. It is obvious that the drawings in the following description only illustrate some embodiments of the present disclosure, and those skilled in the art, without creative work, can also obtain other drawings based on these drawings.

DETAILED DESCRIPTION

In order to make the purpose, technical solutions, and technical effects in the embodiments of the present disclosure more clearly, the present disclosure is described in further detail below by referring to the accompanying drawings and embodiments. It should be understood that specific embodiments described herein are intended to explain the present disclosure only and are not intended to limit the present disclosure. An embodiment or a feature of the present disclosure may be combined with some other embodiments of the present disclosure and/or some other features without conflict.

A detection instrument is provided by some embodiments of the present disclosure. The detection instrument may be configured to inspect a body surface and/or an internal body tissue, so as to obtain an inspection result. Of course, in some application scenarios, the detection instrument may also be configured to inspect an animal body, which is not limited herein.

Figure 1:
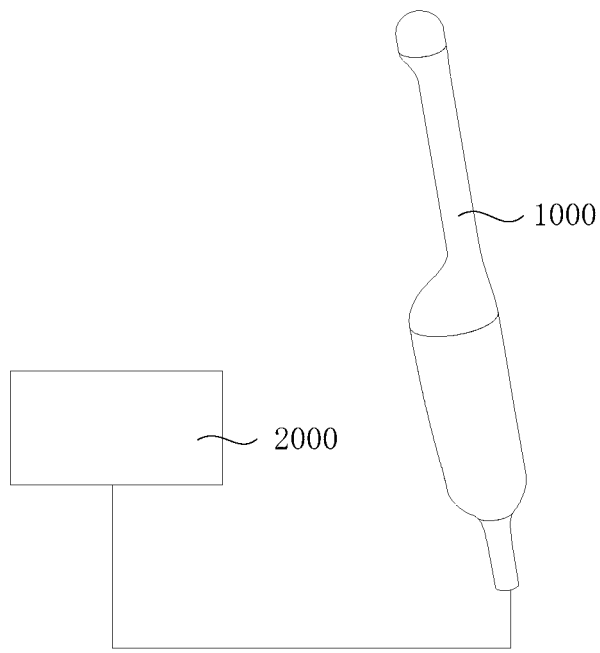
FIG. 1 is a schematic structural view of a detection instrument according to some embodiments of the present disclosure.

As shown in FIG. 1, in an embodiment, the detection instrument may include a detection probe 1000 and a host 2000. The detection probe 1000 may be connected to the host 2000 via a wired/wireless way, so as to detect a part of the human body to be detected under the control of the host 2000.

In some embodiments, the detection probe 1000 may be a three dimensional (hereinafter 3D) mechanical probe, a four dimensional (hereinafter 4D) mechanical probe, etc., that is, an ultrasonic probe with a 3D/4D imaging function. Under the signal control of the host 2000, the detection probe 1000 may transmit an ultrasonic signal to human tissues and receive an echo signal with information of the human tissues. The host 2000 images the human tissues by processing the echo signal of the detection probe 1000, Thus, a 3D/4D image of the human tissues may be constructed for medical analysis, such as using the 3D/4D mechanical probe for gynecological examination or the like.

Of course, the detection probe 1000 may also be used for other purposes, such as sending electrical stimulation to the human tissues, performing physical massage, etc., under the signal control of the host 2000, which is not limited herein.

Figure 2:
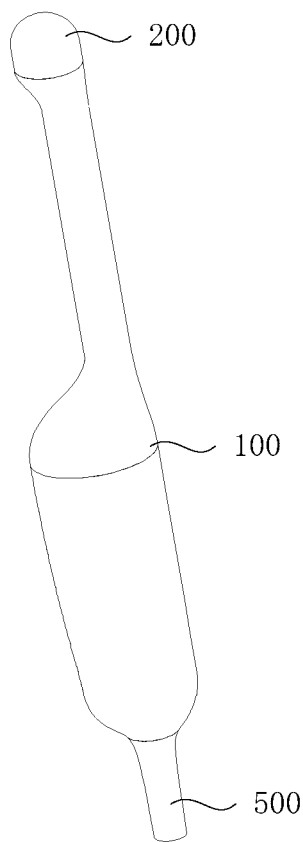
FIG. 2 is a schematic partial structural view of a detection probe according to some embodiments of the present disclosure.
Figure 3:
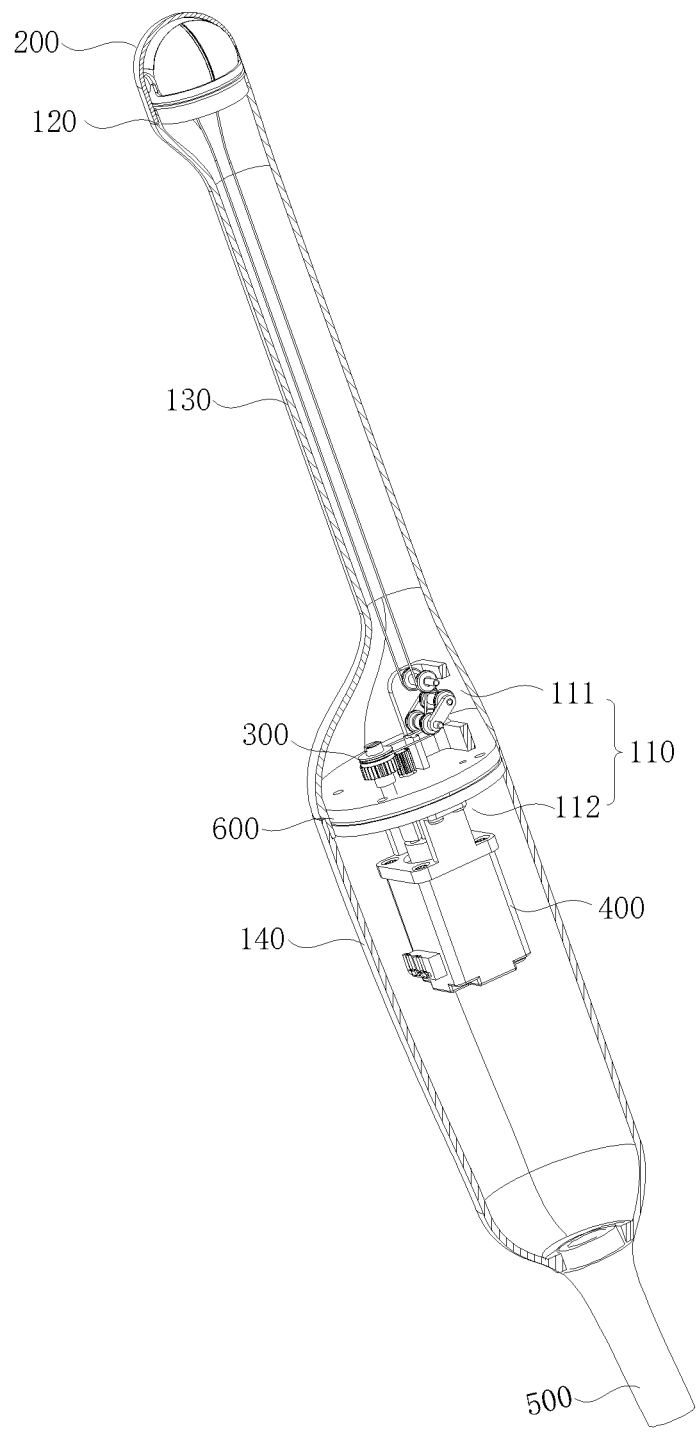
FIG. 3 is a schematic partial structural view of the detection probe according to some embodiments of present disclosure.

In an embodiment, as shown in FIG. 2 and FIG. 3, the detection probe 1000 may include a housing 100, a detection mechanism 200, a transmission device 300, a driving mechanism 400, a tail sleeve assembly 500, a mounting assembly 600, etc. The transmission device 300 may be connected to the driving mechanism 400 and the detection mechanism 200, respectively. The host 2000 may be connected to the driving mechanism 400 and the detection mechanism 200 via the tail sleeve component 500. The host 2000 may control an operation of the driving mechanism 400 to drive the transmission device 300 to drive the detection mechanism 200 to move. The detection mechanism 200 may feed back detected information to the host 2000 for analysis and processing, and a detection result is obtained.

Of course, in other embodiments, the detection probe 1000 may include more or less structures than the above-mentioned structures, which may be selected according to actual needs, and is not limited herein.

In some embodiments, the housing 100 defines a receiving space 110. An opening 120 is defined on an end of the housing 100, and the opening 120 is in communication with the receiving space 110. The receiving space 110 is configured to receive at least part of an internal structure of the detection probe 1000, so as to provide support and protection for the internal structure.

In some embodiments, the housing 100 may be an integral structure, or may be formed by assembling a plurality of different parts respectively. In an embodiment, the housing 100 may include an extension portion 130 and a handheld portion 140. The extension portion 130 and the handheld portion 140 are connected to each other to form the housing 100. In some embodiments, the extension portion 130 may be connected to the handheld portion 140 by at least one of pasting by using adhesive, setting a specific connection structure for snapping, buckling, etc., which is not limited herein.

Accordingly, the extension portion 130 and the handheld portion 140 correspond to an extension area 111 and a receiving area 112 of the receiving space 110, respectively. That is, the extension portion 130 may correspond to the extension area 111, and the handheld portion 140 corresponds to the receiving area 112. The transmission device 300 and the driving mechanism 400 may be received correspondingly in the extension area 111 and the receiving area 112, respectively. That is, the transmission device 300 may be received correspondingly in the extension area 111, and the driving mechanism 400 may be received correspondingly in the receiving area 112. It should be noted that in this embodiment, a corresponding relationship between various areas of the receiving space 110 and various functional mechanisms is not strictly limited. For example, in some application scenarios, the transmission device 300 may be partially received in the extension area 111, and partially received in the receiving area 112, which may be designed according to actual needs.

In some embodiments, a shape, a size, etc. of each part of the housing 100 may be jointly determined according to its own function, and the shape, the size, the function, etc., of the internal structure included in the corresponding area of the receiving space 110.

It should be noted that, in an embodiment, the detection probe 1000 may be extended into the human body cavity to detect internal tissue of the human body. During an operation, the detection mechanism 200 is disposed on a head, an operator holds the handheld portion 140, and extends the detection mechanism 200 into the body through the extension of the extension portion 130 to perform the detection function. In addition, the tail sleeve assembly 500 is disposed outside the human body, and thus it is convenient for the corresponding functional mechanisms of each part to perform a corresponding function.

Figure 4:
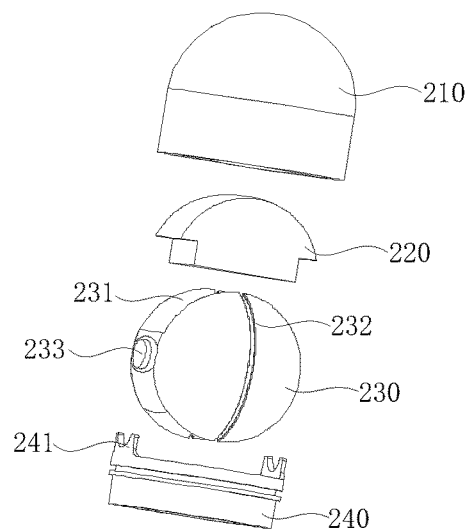
FIG. 4 is a schematic exploded view of a detection mechanism of the detection probe according to some embodiments of the present disclosure.

In some embodiments, as shown in FIG. 4, the detection mechanism 200 may include an acoustic window 210, a transducer 220, an assembly base 230, and a bearing bracket 240.

The transducer 220 may be connected to the host 2000. Based on the control signal transmitted by the host 2000, the transducer 220 may emit ultrasonic waves configured as a detection signal to human tissues to be detected, and may receive a feedback signal carrying detection information.

The acoustic window 210 may have ultrasonic penetrability and be arranged on a periphery of the transducer 220. In some embodiments, the acoustic window 210 may be arranged on the opening 120 disposed on an end of the housing 100, and may be covered outside of the transducer 220, the assembly base 230, and the bearing bracket 240. It should be noted that in practical applications, coupling fluid configured for ultrasonic transmission may be filled between the acoustic window 210 and the transducer 220, thereby achieving the transmission of the ultrasonic detection signal and the reception of the feedback signal with the cooperation of the transducer 220, the coupling fluid, and the acoustic window 210.

An assembly position 231 is defined on the assembly base 230. The assembly position 231 may be configured to accommodate the above-mentioned transducer 220, and the transducer 220 may be arranged on the assembly base 230. In some embodiments, the transducer 220 may be bonded to the assembly position 231 by using adhesive, such as epoxy adhesive, etc. In addition, an assembly groove 232 is defined on each of two sides of the assembly base 230. The assembly groove 232 may be configured to arrange some components of the transmission device 300, thereby achieving connection with the transmission device 300.

The bearing bracket 240 may be configured to support the assembly base 230, thereby supporting the transducer 220. In some embodiments, the bearing bracket 240 may be a ring bracket, such as a circular bracket, a square annular bracket, etc. In some embodiments, a shape of the bearing bracket 240 may match a shape of an inner sidewall disposed on the opening 120 of the housing 100, and the bearing bracket 240 may be arranged on the inner sidewall of the housing 100 at the opening 120.

The bearing bracket 240 may further include two concave-arc bearing tables 241. Each of the two concave-arc bearing tables 241 may have a concave-arc bearing surface. In some embodiments, the assembly base 230 may further include two cylindrical bosses 233 located on two sides of the assembly base 230. Each of the two cylindrical bosses 233 may have an arc-shaped side surface and is configured to be movably supported on the corresponding concave-arc bearing surface of the bearing bracket 240, such that the two cylindrical bosses 233 may oscillate under the support of the concave-arc bearing table 241, and thus when the assembly base 230 is received to a force applied by the transmission device 300, the transducer 220 may be driven to reciprocatingly oscillate in a certain direction.

In some embodiments, as shown in FIG. 3 and FIGS. 5-11, the transmission device 300 may include a gear transmission mechanism 320, a rope transmission mechanism 330, etc.

In some embodiments, the gear rotation mechanism 320 may be connected to the driving mechanism 400 and the rope transmission mechanism 330, respectively, such that the power output by the driving mechanism 400 is received and transmitted to the rope transmission mechanism 330. The rope transmission mechanism 330 is further connected to the detection mechanism 200, and when receiving the power transmitted by the gear transmission mechanism 320, the rope transmission mechanism 330 may drive the detection mechanism 200 to move, thereby realizing the detection.

The transmission device 300 may be arranged in the receiving space 110 via the mounting assembly 600. In some embodiments, the transmission device 300 may be arranged on the inner sidewall of the housing 100. In some embodiments, the mounting assembly 600 may include a mounting base 610, a sealing member 620, a support frame 630, a first shaft 640, a second shaft 650, etc. In some application scenarios, the first shaft 640 or the second shaft 650 may also be referred to as a support shaft, which is not limited herein.

The mounting base 610 may be arranged on the housing 100 and surrounded by the inner sidewall of the housing 100. In some embodiments, the mounting base 610 may be arranged on an end of the extension portion 130 close to the handheld portion 140, and may be bonded by means of adhesive to achieve installation, or installed by means of clamping, interference fit, or the like. In some embodiments, at least part of the appearance of the mounting base 610 may also match a shape of the inner sidewall of the housing 100 at a mounting location, such that a connection between the mounting base 610 and the inner sidewall of the housing 100 is sealed, and thus separating the extension area 111 of the receiving space 110 from the receiving area 112.

In some embodiments, the mounting base 610 defines a mounting hole 611 penetrating the mounting base 610. The extension area 111 and the receiving area 112 disposed on the two sides of the mounting base 610 may be in communication with each other via the mounting hole 611. In some embodiments, the sealing member 620 may be arranged in the mounting hole 611.

The support frame 630 may be connected to a side of the mounting base 610 facing the rope transmission mechanism 330, and may extend along a direction substantially perpendicular to and away from a main surface of the mounting base 610.

The first shaft 640 and the second shaft 650 may be connected to and arranged on the support frame 630, and may be spaced apart from each other. In some embodiments, two ends of the first shaft 640 and the second shaft 650 may be fixedly connected to the support frame, and the first shaft 640 and the second shaft 650 may be arranged in parallel with each other. In some embodiments, the first shaft 640 and the second shaft 650 may be further parallel to the main surface of the mounting base 610, which is not limited herein.

The mounting base 610, the support frame 630, the first shaft 640, and the second shaft 650 may be independent structures respectively, and may be connected together by means of bonding, clamping, screwing, plugging, etc. In some embodiments, the mounting base 610, the support frame 630, the first shaft 640, and the second shaft 650 may also be an integral structure in whole or in part, which is not limited herein.

In some embodiments, the gear transmission mechanism 320 and the rope transmission mechanism 330 may be arranged on the inner sidewall of the housing 100 via the mounting assembly 600 on a side of the extension area 111.

The gear transmission mechanism 320 may have various forms, as long as the gear transmission mechanism 320 may transmit the power output by the driving mechanism 400 to the rope transmission mechanism 330.

Figure 5:
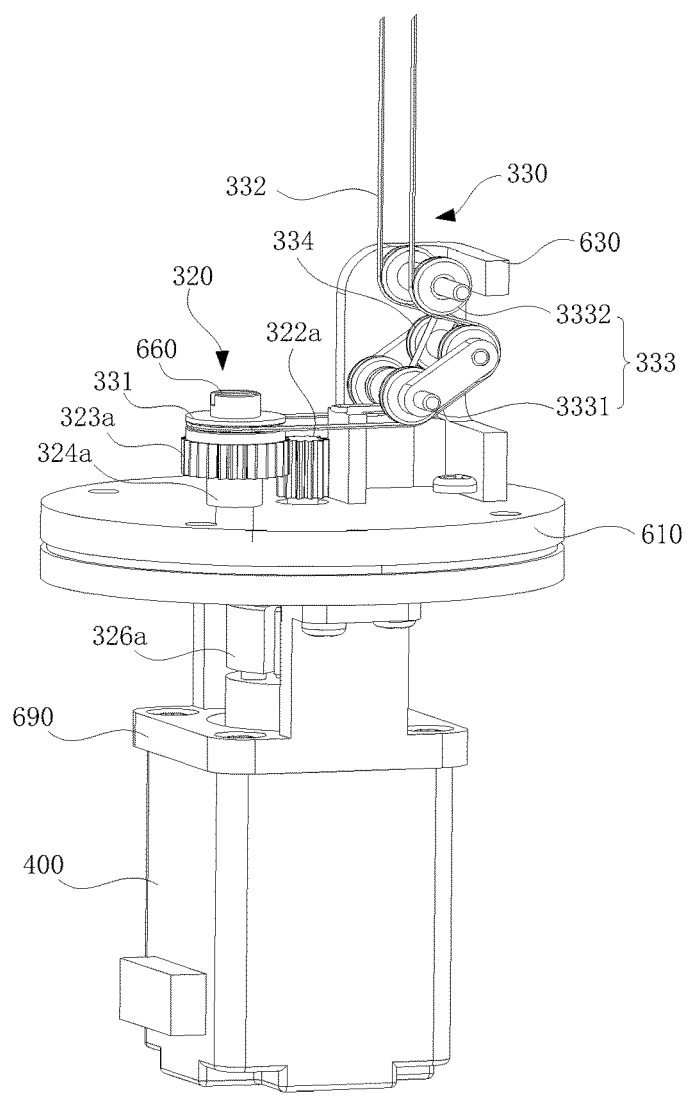
FIG. 5 is a schematic structural view of a transmission mechanism and a driving mechanism of the detection probe according to some embodiments of the present disclosure.
Figure 8:
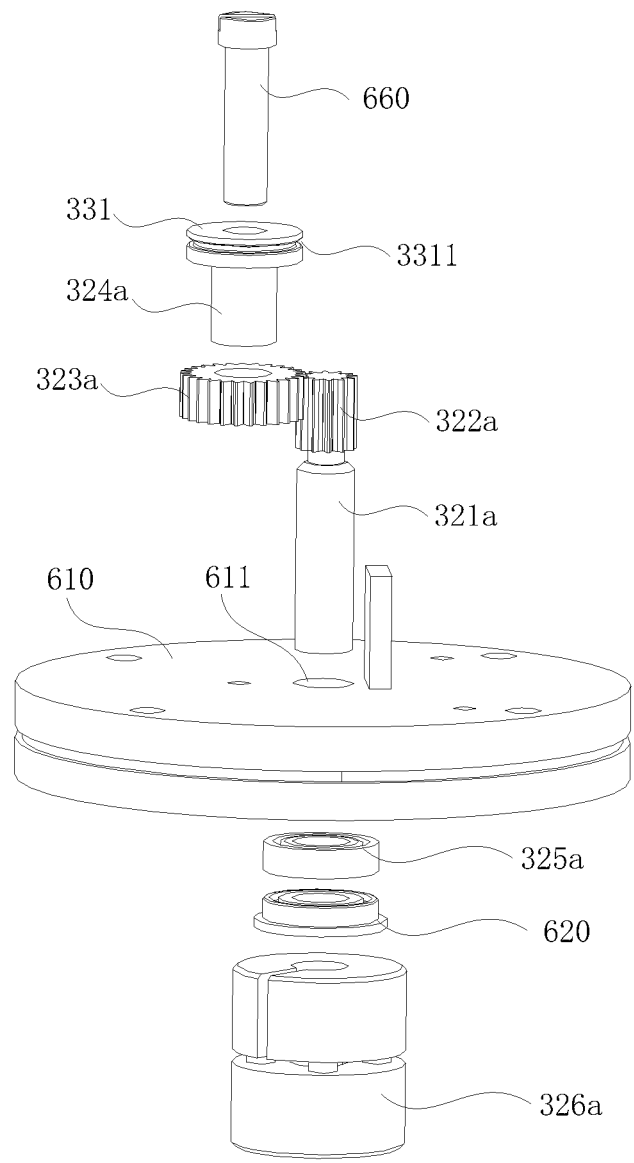
FIG. 8 is a partially exploded schematic structural view of the detection probe according to some embodiments of present disclosure.

In an embodiment, as further shown in FIG. 3, FIG. 5 and FIG. 8, the gear transmission mechanism 320 may include a driving shaft 321a, a driving gear 322a, a driven gear 323a, a driven shaft 324a, a first bearing 325a, a shaft coupling 326a, etc.

One end of the driving shaft 321a is disposed on the extension area 111, and the other end of the driving shaft 321a passes through the mounting hole 611 of the mounting base 610 and enters the receiving area 112, and is connected to the shaft coupling 326a. In this way, the other end of the driving shaft 321a is connected to an output end of the driving mechanism 400 via the shaft coupling 326a, such that the driving mechanism 400 may drive the driving shaft 321a to rotate.

In some embodiments, the first bearing 325a may be sleeved on a periphery of the driving shaft 321a and may be arranged in the mounting hole 611, so as to support the rotation of the driving shaft 321a. The sealing member 620 may be an oil seal, such as a skeleton oil seal or the like. In some embodiments, the sealing member 620 may be sleeved on the periphery of the driving shaft 321a and arranged in the mounting hole 611, and configured to seal the mounting hole 611, thereby further separating the extension area 111 from the receiving area 112.

The driving gear 322a is arranged on an end of the driving shaft 321a disposed on the extension area 111, and is driven to rotate synchronously with the driving shaft 321a by the driving mechanism 400. It should be noted that the driving gear 322a and the driving shaft 321a may be independent structures and connected to each other in a certain way. In some embodiments, the driving gear 322a and the driving shaft 321a may also be an integrated structure, that is, the driving shaft 321a and the driving gear 322a together form a gear shaft, which may be selected according to actual needs.

The driven gear 323a is engaged with the driving gear 322a, and rotates with the driving gear 322a. The driving gear 322a and the driven gear 323a may be cylindrical gears that are arranged in parallel along an axial direction. In practical applications, the driving gear 322a and the driven gear 323a with appropriate numbers of teeth may be selected according to the needs. For example, the number of teeth of the driven gear 323a may be greater than that of the driving gear 322a, such that it may achieve deceleration motion through gear transmission and amplify transmitted power, thereby increasing a torque which is configured to drive the transducer 220 to oscillate. In addition, since the larger the output torque of the driving mechanism 400, the larger the volume and weight, the setting of the above-mentioned gear transmission mechanism 320 may also increase the oscillate torque of the transducer 220 without increasing the volume and weight of the driving mechanism 400, thereby improving the portability of the detection probe 1000.

In some embodiments, the driven shaft 324a is respectively connected to the driven gear 323a and an input end of the rope transmission mechanism 330, so as to rotate synchronously with the driven gear 323a, and to cause the input end of the rope transmission mechanism 330 to move under the drive of the driven shaft 324a.

In some embodiments, the mounting assembly 600 may further include the mounting shaft 660. The mounting shaft 660 may be connected to and arranged on the side of the mounting base 610 facing the gear transmission mechanism 320, and may extend along a direction substantially perpendicular to and away from a main surface of the mounting base 610. The mounting shaft 660 and the support frame 630 may be arranged on the same side of the mounting base 610 and spaced apart from each other.

In some embodiments, the driven shaft 324a may be a hollow shaft, inserted in a center of driven gear 323a, and sleeved on a periphery of mounting shaft 660, such that the driven shaft 324a may be driven to rotate around the mounting shaft 660 by the driven gear 323a.

Figure 6:
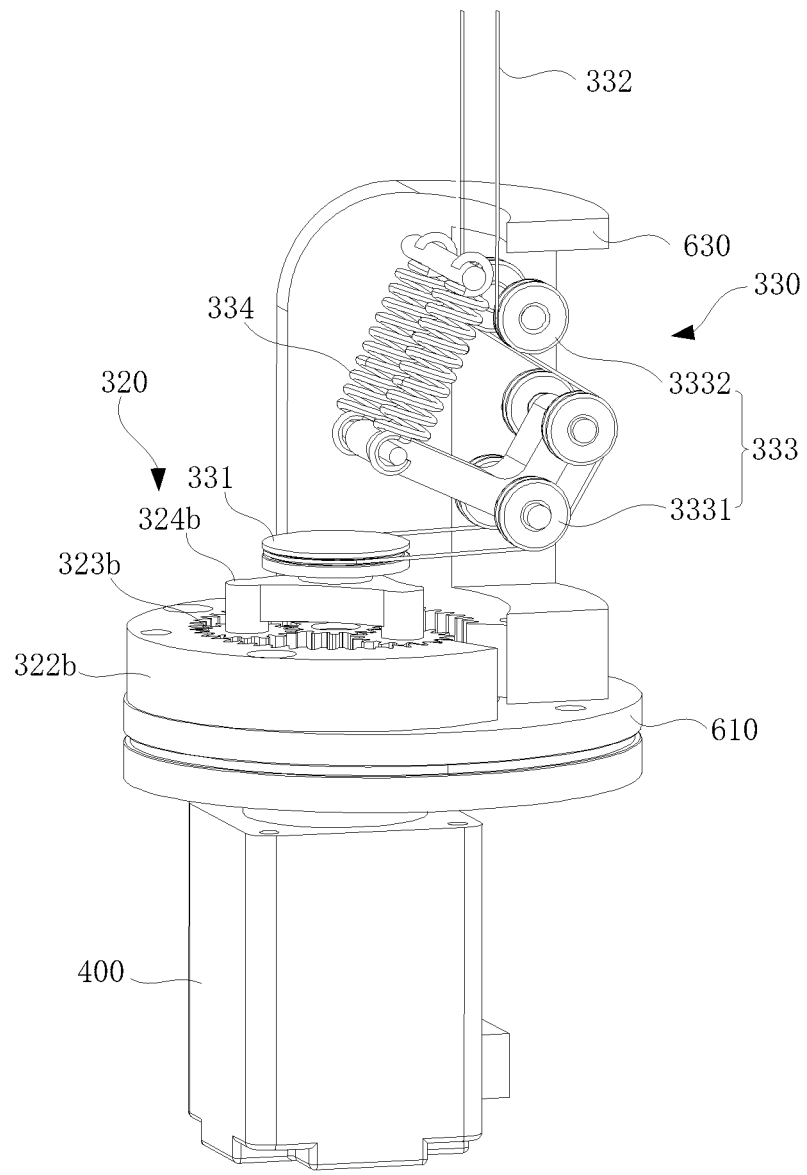
FIG. 6 is a schematic structural view of the transmission mechanism and the driving mechanism of the detection probe according to some embodiments of present disclosure.
Figure 9:
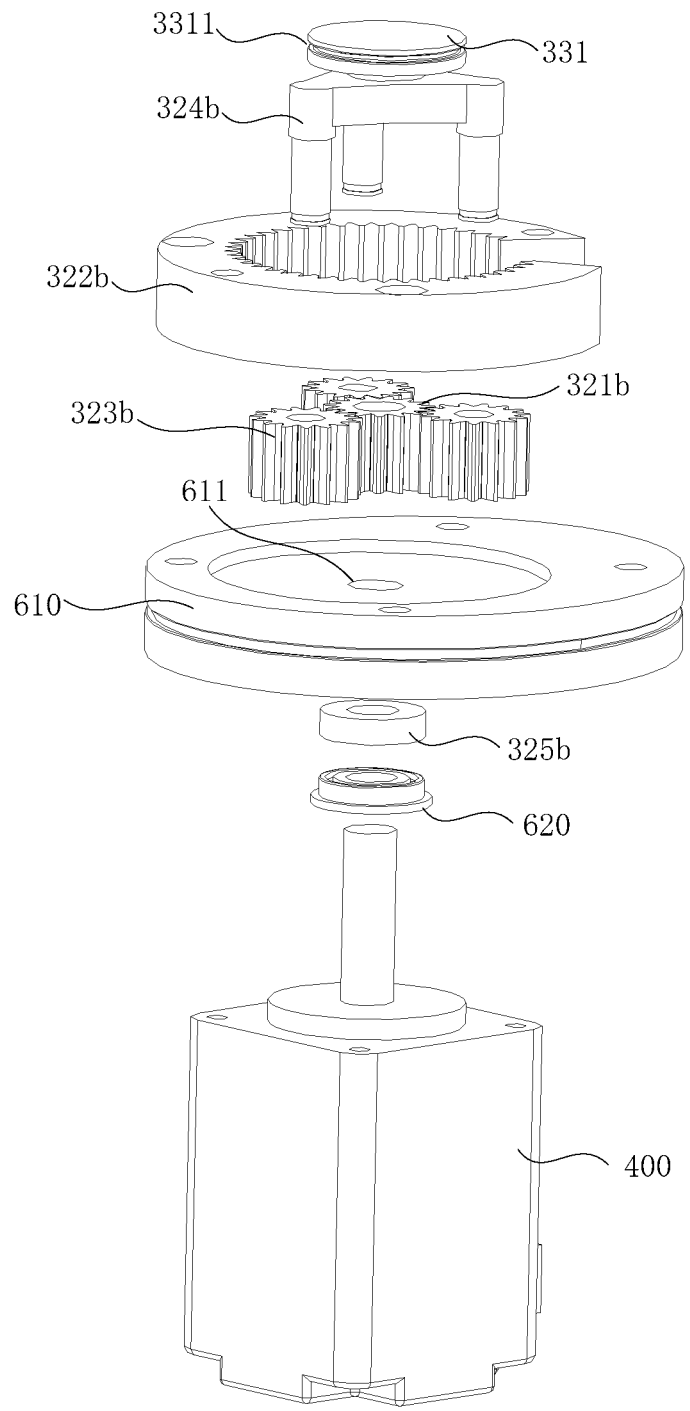
FIG. 9 is a partially exploded schematic structural view of the detection probe according to some embodiments of present disclosure.

In some embodiments, as further shown in FIG. 3, FIG. 6, and FIG. 9, the gear transmission mechanism 320 may be in a form of a planetary gear transmission. In some embodiments, the gear transmission mechanism 320 may include a sun gear 321b, a ring gear 322b, a plurality of planetary gears 323b, a planetary carrier 324b, a second bearing 325b, and the like.

The output end of the driving mechanism 400 passes through the mounting hole 611 of the mounting base 610 from the receiving area 112, enters the extension area 111, and is connected to the sun gear 321b. In addition, the output end of the driving mechanism 400 is configured as a rotatory shaft of the sun gear 321b and drives the sun gear 321b to rotate. The second bearing 325b may be sleeved on a periphery of the output end of the driving mechanism 400 and arranged in the mounting hole 611, so as to support the rotation of the output end of the driving mechanism 400. The sealing element 620 may be an oil seal, such as a skeleton oil seal or the like. In some embodiments, the sealing member 620 may be sleeved on the periphery of the output end of the driving mechanism 400 and arranged in the mounting hole 611, and configured to seal the mounting hole 611, thereby further separating the extension area 111 from the receiving area 112.

The ring gear 322b may be arranged on the mounting base 610, sleeved on the periphery of the sun gear 321b, arranged coaxially with the sun gear 321b, and spaced apart from the sun gear 321b. The number of teeth and a size of the ring gear 322b may be designed according to actual needs.

The number of the planetary gears 323b may also be designed according to actual needs. In the embodiment, the number of the planetary gears 323b may be three. The three planetary gears 323b are arranged between the sun gear 321b and the ring gear 322b, and spaced apart from each other. One side of each of the plurality of planetary gears 323b is engaged with the sun gear 321b, and the other side of the each of the plurality of planetary gears 323b is engaged with an inner side of the ring gear 322b, such that the each of the plurality of planetary gears 323b may rotate in the ring gear 322b with the sun gear 321b.

The planetary carrier 324b may be connected to a side of the each of the plurality of planetary gears 323b away from the mounting base 610, and driven to rotate coaxially with the sun gear 321b by the planetary gear 323b. The planetary carrier 324b may be further connected to the input end of the rope driving mechanism 330, thereby outputting the power received by the sun gear 321b to the input end of the rope driving mechanism 330, and thus the input end of the rope driving mechanism 330 is driven to move.

For two above-mentioned implementation methods of the gear transmission mechanism 320, in a first method, the driving gear 322a and the driven gear 323a may both be cylindrical gears, which have a high power transmission reliability, a high transmission efficiency (i.e., reaching more than 0.99), a long gear life, a simple and compact structure, and a simple operation and maintenance. For a second planetary transmission method, it has a compact structure, a small size, a light weight, a large transmission ratio, a good coaxiality, and a high transmission efficiency. In practical applications, either of the two methods may be selected according to the needs, or the combination of the two methods may be used, which is not limited herein.

In some embodiments, as further shown in FIGS. 5-6 and FIGS. 10-11, the rope transmission mechanism 330 may include a rope pulley 331, a rope 332, a reversing assembly 333, a tensioning assembly 334, and a stabilizing pulley group 335, etc.

The rope pulley 331 may be connected to an output end of the gear transmission mechanism 320 and rotate with the output end of the gear transmission mechanism 320. The rope 332 is wound on the periphery of the rope pulley 331 and connected to the assembly base 230 of the detection mechanism 200 via the reversing assembly 333 and the tensioning assembly 334, thereby driving the transducer 220 arranged on the assembly base 230 to oscillate.

In some embodiments, two ends of the rope 332 are respectively arranged in the corresponding assembly grooves 232 of the assembly base 230 in one-to-one correspondence.

In some embodiments, a guiding groove 3311 may be further defined on the periphery of the rope pulley 331. The guiding groove 3311 may surround the periphery of the rope pulley 331 and be recessed. The rope 332 may be wound in the guiding groove 3311, thereby maintaining synchronous motion with the rope pulley 331.

In some embodiments, for the above-mentioned first method of the gear transmission mechanism 320, as shown in FIGS. 5 and 8, the driven shaft 324a is configured as the output end of the gear transmission mechanism 320, and the rope pulley 331 may be sleeved on a periphery of the driven shaft 324a and synchronously rotate accordingly. In the embodiment, the driven shaft 324a is not only configured as the driven shaft of the driven gear 323a, but also configured as the driving shaft of the rope pulley 331.

In an application scenario, the rope pulley 331 is integrally connected to an end of the driven shaft 324a, and the driven shaft 324a is connected to the driven gear 323a in a split mode. Of course, in other application scenarios, the driven shaft 324a may also be integrated with the driven gear 323a, and connected to the rope pulley 331 in a split mode, which is not limited herein.

For the above-mentioned second method of the gear transmission mechanism 320, as shown in FIGS. 6 and 9, the planetary carrier 324b is configured as the output end of the gear transmission mechanism 320 and is connected to the rope pulley 331. In some embodiments, the planetary carrier 324b may be connected to a center of the rope pulley 331 and drive the rope pulley 331 to rotate synchronously and coaxially. In an application scenario, the rope pulley 331 may be connected to an end of the planetary carrier 324b away from the planetary carrier 323b, and is integrated with the planetary carrier 324b. Of course, in other application scenarios, the rope pulley 331 and the planetary carrier 324b may also be separate structures, which is not limited herein.

It should be noted that the reciprocating oscillation of the transducer 220 is driven by the driving mechanism 400. However, in some application scenarios, due to factors such as structural and spatial limitations, a driving direction of the output end of the driving mechanism 400 is not consistent with an oscillate direction required by the transducer 220. Therefore, the transmission device 300 may be designed to change a direction of power transmission during a transmission process, such that the transmission direction of the output end of the rope transmission mechanism 330 is consistent with the oscillate direction required by the transducer 220. In some embodiments, a structure that changes the transmission direction may be arranged on the gear transmission mechanism 340, or arranged on the rope transmission mechanism 330, or arranged on both the gear transmission mechanism 340 and the rope transmission mechanism 330.

In the embodiment, the reversing assembly 333 may be arranged between the rope pulley 331 and the detection mechanism 200 along an extension path of the rope 332. During the transmission process, a transmission direction of the rope 332 is changed, such that it may be possible to ensure that a transmission direction of two ends of the rope 332 connecting the assembly base 230 is consistent with a movement direction required by the detection mechanism 200.

In some embodiments, the reversing assembly 333 may include a first reversing pulley group including two first reversing pulleys 3331 and a second reversing pulley group including two second reversing pulleys 3332. The two first reversing pulleys 3331 may be rotated and sleeved on a periphery of the first shaft 640, respectively, and are spaced apart from each other. The two second reversing pulleys 3332 may be rotated and sleeved on a periphery of the second shaft 650, respectively, and are spaced apart from each other.

Of course, in other embodiments, the reversing pulley assembly 333 may further include more reversing pulley groups, such as three groups, four groups, five groups, etc., which may be selected according to actual needs and is not limited herein.

In some embodiments, along the extension path, each of two sides of the rope 332 is sequentially wound on a corresponding periphery of each of the first reversing pulley 3331 and the second reversing pulley 3332 in a staggered mode. The transmission direction is changed under an action of the first reversing pulley 3331 and the second reversing pulley 3332.

In some embodiments, the tensioning assembly 334 may be arranged between the rope pulley 331 and the detection mechanism 200 along the extension path of the rope 332. In some embodiments, the tensioning assembly 334 may apply a force to the rope 332 at a location between the two reversing pulley groups, such that the rope 332 may be in a tensioned state, thereby enabling the rope transmission mechanism 330 to drive the transducer 220 to oscillate smoothly. In this way, it may be possible to enable the detection probe 1000 to perform smooth scanning and detection, thereby improving the accuracy of the detection result.

In some embodiments, the tensioning assembly 334 may include a tensioning adjusting seat 3341, a tensioning pulley 3343, and a force applying member 3344.

The tensioning adjustment base 3341 may be rotatably sleeved on the periphery of the first shaft 640, such that when the tensioning adjustment base 3341 is under force, the tensioning adjustment base 3341 may rotate around the first shaft 640 for adjustment, and thus the tensioning adjustment base 3341 is in a balanced state.

Figure 10:
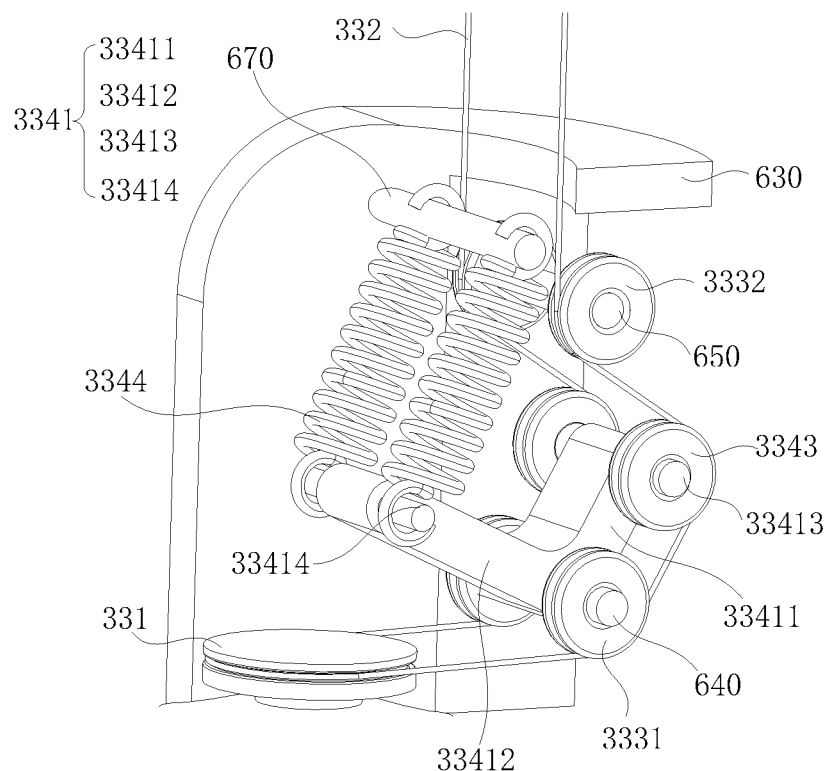
FIG. 10 is a schematic partial structural view of a rope transmission mechanism of the detection probe according to some embodiments of present disclosure.
Figure 11:
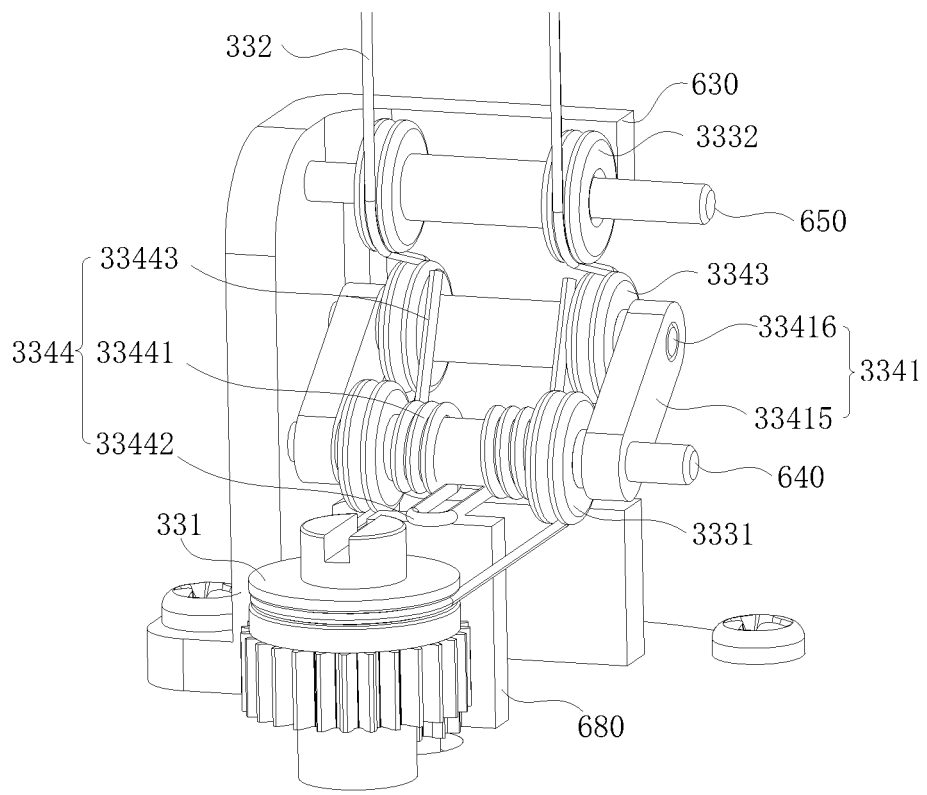
FIG. 11 is a schematic partial structural view of the rope transmission mechanism of the detection probe according to some embodiments of present disclosure.

In some embodiments, the tensioning adjustment base 3341 may be sleeved on the periphery of the first shaft 640 between two first reversing pulleys 3331, as shown in FIG. 10. Alternatively, the tensioning adjustment base 3341 may be sleeved on the periphery of the first shaft 640 on two sides of two first reversing pulleys 3331, as shown in FIG. 11. The present disclosure is not limited herein.

In some embodiments, the number of tensioning pulleys 3343 may be one or more. When the number of tensioning pulleys 3343 is one, a shape of the tensioning pulley 3343 may be a long column, and two accommodating grooves are defined on a surface of the tensioning pulley 3343. The two accommodating grooves are axially arranged and surrounding the tensioning pulley 3343. The two sides of the rope 332 may be wound on the periphery of the tensioning pulley 3343 by being respectively wound in the corresponding accommodating grooves.

In the embodiment, the number of tensioning pulleys 3343 is two, and one accommodating groove is defined on a surface of each of the two tensioning pulleys 3343 and wound on the corresponding tensioning pulley 3343. The two sides of the rope 332 may be wound on the periphery of the tensioning pulley 3343 by being respectively wound in the corresponding accommodating grooves. That is, one of the two sides of the rope 332 may be wound on the periphery of the tensioning pulley 3343 by being respectively wound in the one of corresponding accommodating grooves, and the other one of the two sides of the rope 332 may be wound on the periphery of the tensioning pulley 3343 by being respectively wound in the other one of corresponding accommodating grooves. The two tensioning pulleys 3343 may be spaced apart from each other and are rotatably connected to the tensioning adjustment base 3341.

The force applying member 3344 may be configured to apply tensioning adjustment force to the tensioning adjustment base 3341, such that the tensioning adjustment base 3341 rotates around the first shaft 640, and applies force to the rope 332 via the two tensioning pulleys 3343, and thus the rope 332 may be in the tensioned state.

In an embodiment, after the rope 332 bypasses the rope pulley 331, the two ends of the rope 332 may be further wound on the corresponding periphery of each of the first reversing pulley 3331, the tensioning pulley 3343 and the second reversing pulley 3332 in sequence, and thus the rope 332 is connected to the transducer 220. In this way, on the one hand, the transmission direction is changed via the first reversing pulley 3331 and the second reversing pulley 3332 to meet the requirements. On the other hand, under the action of the tensioning pulley 3343, the rope 332 is in the tensioned state, and thus the oscillation of the transducer 220 may performed smoothly.

A specific structure of the tensioning assembly 334 may be in various forms, as long as the structure may make the rope 332 in the tensioned state.

In an embodiment, as further shown in FIG. 6 and FIG. 10, the tensioning adjustment base 3341 may include a first adjusting arm 33411, a second adjusting arm 33412, a first tensioning pulley shaft 33413, and a connecting rod 33414.

In some embodiments, the first adjusting arm 33411 and the second adjusting arm 33412 may be crosswise connected to each other. In an embodiment, the first adjusting arm 33411 and the second adjusting arm 33412 may be arranged in a "V" shape. The tensioning adjustment base 3341 may be rotatably connected to the first shaft 640 at a connection between the first adjusting arm 33411 and the second adjusting arm 33412. In some embodiments, the tensioning adjustment base 3341 is rotatably sleeved on the periphery of the first shaft 640 at the connection.

The first tensioning pulley shaft 33413 may be connected to an end of the first adjusting arm 33411 away from the second adjusting arm 33412. The two tensioner pulleys 3343 may be rotatably sleeved on the first tensioning pulley shaft 33413 respectively, and may be spaced apart from each other.

In some embodiments, the mounting assembly 600 may further include a fixing rod 670 fixedly connected to a support member 680. The fixing rod 670 may be parallel to and spaced apart from the first shaft 640 and the second shaft 650.

In some embodiments, the force applying member 3344 may include two stretching elastic members, one end of each of the stretching elastic members is connected to the fixing rod 670, and the other end of each of the stretching elastic members is connected to the connecting rod 33414 and configured to apply the tensioning adjustment force to the connecting rod 33414. In this way, the tensioning adjustment base 3341 rotates around the first rotation shaft 640, the two tensioning pulleys 3343 adaptively rotate around the first tensioning pulley shaft 33413 and apply the force to the rope 332, and thus the rope 332 is in the tensioned state.

The two ends of each of the two stretching elastic members may be hooked on the fixing rod 670 and the connecting rod 33414 by means of hooking, respectively. In some embodiments, the two stretching elastic members may be stretching springs.

In some embodiments, as further shown in FIG. 5 and FIG. 11, the tensioning adjustment base 3341 may include a rotating arm 33415 and a second tensioning pulley shaft 33416. One end of the rotating arm 33415 is rotatably connected to the first shaft 640, and the other end of the rotating arm 33415 is connected to the second tensioning pulley shaft 33416, such that the second tensioning pulley shaft 33416 and the first shaft 640 are spaced apart from each other. The two tensioning pulleys 3343 are rotatably sleeved on the second tensioning pulley shaft 33416, respectively.

In some embodiments, the mounting assembly 600 further includes a support member 680 connected to the mounting base 610.

The force applying member 3344 may be a torsional elastic member, and include a torsional elastic portion 33441, a first support end 33442, and a second support end 33443. The torsional elastic portion 33441 may be sleeved on the periphery of the first shaft 640. The first support end 33442 may be connected to one side of the torsional elastic portion 33441 and abut against the support member 680. The second support end 33443 may be connected to the other side of the torsional elastic portion 33441 and abut against the second tensioning pulley shaft 33416. In this way, it may be possible to apply the tensioning adjustment force to the second tensioning pulley shaft 33416 under the elastic force of the torsional elastic portion 33441, such that the tensioning adjustment base 3341 rotates around the first rotation shaft 640, the two tensioning pulleys 3343 may adaptively rotate around the first tensioning pulley shaft 33413 and apply the force to the rope 332, and thus the rope 332 is in the tensioned state.

The components of the tensioning adjustment base 3341 in the above-mentioned embodiments may be independent structures and connected together via a specific connection method, or may also be an overall structure, which is not limited herein.

Figure 12:
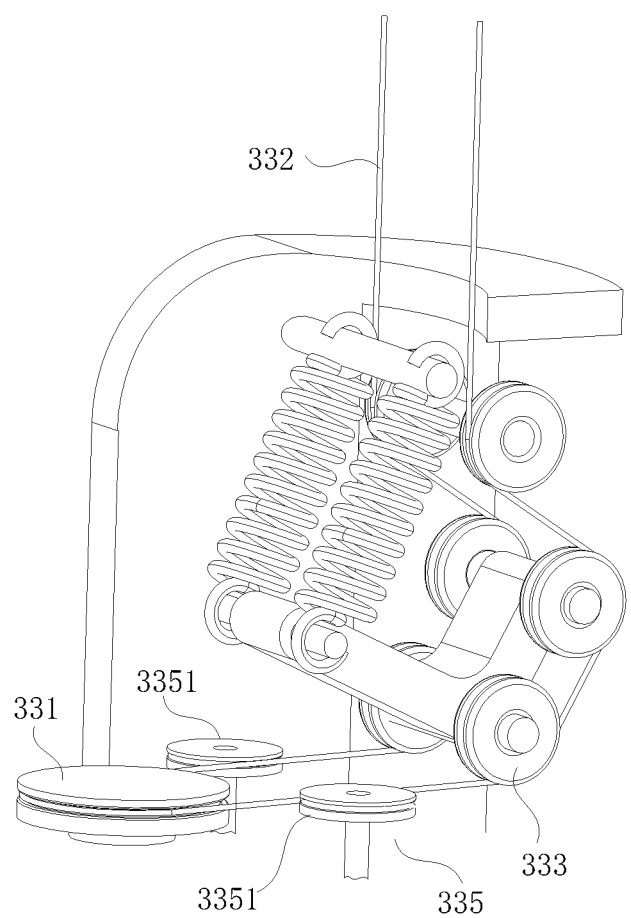
FIG. 12 is a schematic partial structural view of the rope transmission mechanism of the detection probe according to some embodiments of present disclosure.

In some embodiments, as shown in FIG. 12, the stabilizing pulley group 335 may be arranged between the rope pulley 331 and the reversing assembly 333 along the extension path of the rope 332. The stabilizing pulley group 335 may include two stabilizing pulleys 3351.

In some embodiments, the two stabilizing pulleys 3351 may be spaced apart from each other, and a transmission direction of the two stabilizing pulleys 3351 may be consistent with the transmission direction of the rope pulley 331. In some embodiments, after the rope 332 bypasses the rope pulley 331, the two sides of the rope 332 may be respectively wound on the corresponding periphery of each of the two stabilizing pulleys 3351 between the two stabilizing pulleys 3351.

It should be noted that the stabilizing pulley group 335 may play a certain supporting role on a transmission path of the rope 332, thereby making the transmission of the rope 332 more stable and improving the accuracy of the detection result.

It should be noted that, in some embodiments, the transmission device 300 is not limited to the above-mentioned structure. For example, in an application scenario, the mounting base 610, the support frame, etc., of the mounting assembly 600 may also be configured as a part of the transmission device 300. In another application scenario, the transmission device 300 may not include the shaft coupling 326a, etc. A structure of the transmission device 300 may be designed according to the actual needs, which is not limited herein.

Figure 7:
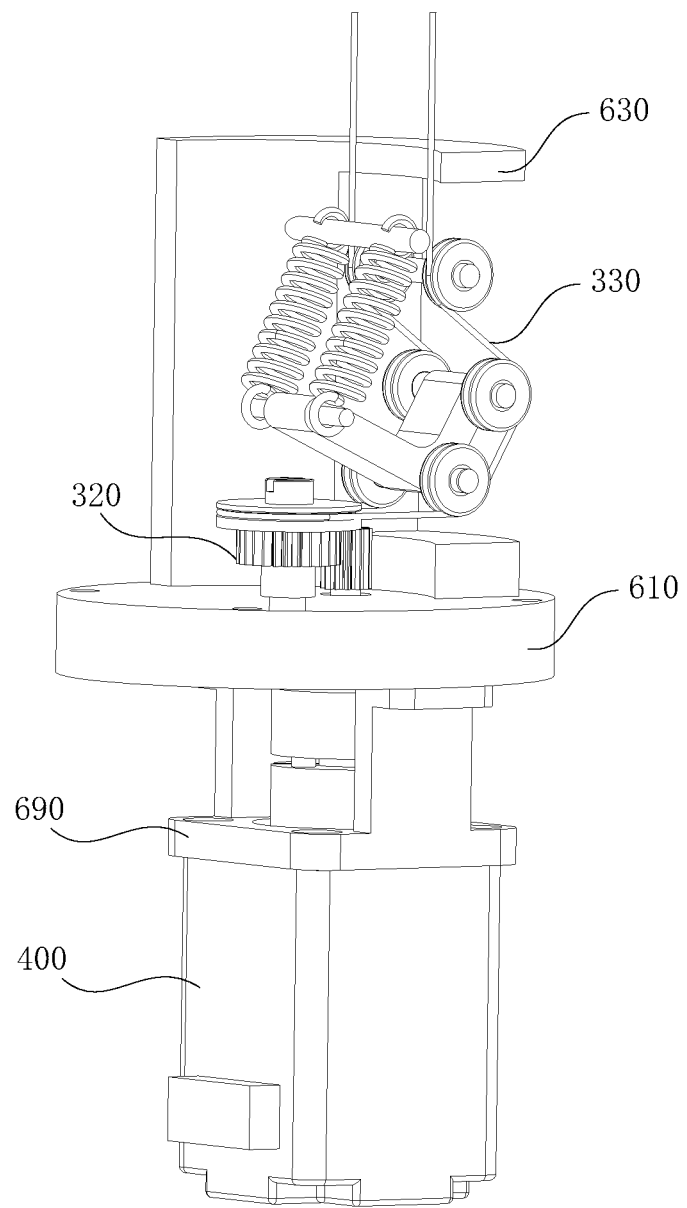
FIG. 7 is a schematic structural view of the transmission mechanism and the driving mechanism of the detection probe according to some embodiments of present disclosure.

In some embodiments, as further shown in FIG. 5 and FIG. 7, the mounting assembly 600 may further include a mounting bracket 690. The mounting bracket 690 may be arranged on a side of the mounting base 610 away from the support frame 630. The driving mechanism 400 may be arranged on the mounting bracket 690.

In some embodiments, the driving mechanism 400 may be a motor, such as a stepping motor. The driving mechanism 400 may output the power to the gear transmission mechanism 320 via the output end.

In some embodiments, as shown in FIGS. 1-3, the tail sleeve assembly 500 may include a circuit structure for the detecting probe 1000 to operate. The host 2000 may be connected to the detection mechanism 200, the driving mechanism 400, etc., of the detection probe 1000 by connecting to the circuit of the tail sleeve assembly 500, thereby achieving signal control and power and data transmission.

According to a first aspect of the embodiments of the present disclosure, a detection probe is provided. The detection probe includes: a housing, defining a receiving space; a detection mechanism, disposed on an end of the housing and configured to perform a detection function; a driving mechanism, disposed in the receiving space and configured to output power; a rope transmission mechanism, disposed in the receiving space and including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups; and a gear transmission mechanism, disposed in the receiving space and connected to the driving mechanism and the rope transmission mechanism respectively, so as to receive the power output by the driving mechanism and transmit the power to the rope transmission mechanism.

In some embodiments, the rope transmission mechanism further includes: a tensioning assembly, arranged on the extension path of the rope and configured to apply force to the rope to make the rope in a tensioned state.

In some embodiments, the detection probe further includes a support shaft connected to the housing; and the tensioning assembly includes: a tensioning adjustment base, rotatably connected to the support shaft; a tensioning pulley, rotatably connected to the tensioning adjustment base, where the rope is wound on a periphery of the tensioning pulley, respectively; and a force applying member, configured to apply a tensioning adjustment force to the tensioning adjustment base, such that the tensioning adjustment base rotates around the support shaft, and applies force to the rope through the tensioning pulley to make the rope in the tensioned state.

In some embodiments, the number of the tensioning pulleys is two; and the tensioning adjustment base includes: a first adjusting arm; a second adjusting arm, connected to the first adjusting arm, where the tensioning adjustment base is rotatably connected to the support shaft at a connection between the first adjusting arm and the second adjusting arm; and a first tensioning pulley shaft, connected to an end of the first adjusting arm away from the second adjusting arm, where two tensioning pulleys are rotatably sleeved on the first tensioning pulley shaft, respectively; where the force applying member is connected to an end of the second adjusting arm away from the first adjusting arm, and is configured to apply the tensioning adjustment force to the end of the second adjusting arm away from the first adjusting arm, such that the tensioning adjustment base rotates around the support shaft, the two tensioning pulleys adaptively rotate around the first tensioning pulley shaft and apply force to the rope, and the rope is in the tensioned state.

In some embodiments, the detection probe further includes a fixing rod connected to the housing, and the tensioning adjustment base further includes a connecting rod arranged at the end of the second adjusting arm away from the first adjusting arm; the force applying member includes two stretching elastic members, one end of each of the stretching elastic members is connected to the fixing rod, and the other end of each of the stretching elastic members is connected to the connecting rod and configured to apply the tensioning adjustment force to the connecting rod.

In some embodiments, the number of the tensioning pulleys is two; and the tensioning adjustment base includes: a rotating arm, an end of the rotating arm being rotatably connected to the support shaft; and a second tensioning pulley shaft, arranged at an end of the rotating arm away from the support shaft, where two tensioning pulleys are rotatably sleeved on the second tensioning pulley shaft, respectively. The force applying member is connected to the second tensioning pulley shaft and is configured to apply the tensioning adjustment force to the second tensioning pulley shaft, such that the tensioning adjustment base rotates around the support shaft, the two tensioning pulleys adaptively rotate around the second tensioning pulley shaft and apply force to the rope, and the rope is in the tensioned state.

In some embodiments, the detection probe further includes a support member connected to the housing; and the force applying member is a torsional elastic member, and includes: a torsional elastic portion, sleeved around a periphery of the support shaft; a first support end, connected to one side of the torsional elastic portion and abutting against the support member; and a second support end, connected to the other side of the torsional elastic portion, abutting against the second tensioning pulley shaft, and applying the tensioning adjustment force to the second tensioning pulley shaft under an elastic force of the torsional elastic portion.

In some embodiments, the detection probe further includes a first shaft and a second shaft which are connected to the housing and spaced apart from each other; and the two reversing pulley groups include: two first reversing pulleys, rotatably sleeved on a periphery of the first shaft respectively, and spaced apart from each other; and two second reversing pulleys, rotatably sleeved on a periphery of the second shaft respectively, and spaced apart from each other; where along the extension path, the rope is sequentially wound on a corresponding periphery of each of the first reversing pulley and the second reversing pulley in a staggered mode, so as to change the transmission direction.

In some embodiments, the rope transmission mechanism further includes: a rope pulley, where the rope is wound on a periphery of the rope pulley; a stabilizing pulley group, arranged between the rope pulley and the reversing assembly along the extension path of the rope, and including two stabilizing pulleys spaced apart from each other, where two sides of the rope are respectively wound on peripheries of the corresponding stabilizing pulleys between the two stabilizing pulleys.

In some embodiments, the rope transmission mechanism further includes a rope pulley, and the rope is wound on a periphery of the rope pulley; and the gear transmission mechanism includes: a driving shaft, connected to the driving mechanism and rotating under driving of the driving mechanism; a driving gear, arranged on an end of the driving shaft and rotating synchronously with the driving shaft; a driven gear, engaged with the driving gear and rotating with the driving gear; and a driven shaft, connected to the driven gear and the rope pulley respectively, moving synchronously with the driven gear, driving the rope pulley to rotate, and the rope driving the detection mechanism to move with a rotation of the rope pulley.

In some embodiments, the detection probe further includes: a shaft coupling, an end of the shaft coupling being connected to the driving mechanism, and the other end of the shaft coupling being connected to the driving shaft, so as to transmit the power output by the driving mechanism to the driving shaft.

In some embodiments, the rope transmission mechanism further includes a rope pulley, and the rope is wound on a periphery of the rope pulley; and the gear transmission mechanism includes: a sun gear, connected to the driving mechanism and rotating under driving of the driving mechanism; a ring gear, sleeved on a periphery of the sun gear, arranged coaxially with the sun gear, and spaced apart from the sun gear; a plurality of planetary gears, arranged between the sun gear and the ring gear, and spaced apart from each other, where one side of each of the plurality of planetary gears is engaged with the sun gear, and the other side of each of the plurality of planetary gears is engaged with an inner side of the ring gear, such that the plurality of planetary gears rotate with the sun gear; and a planetary carrier, connected to the plurality of planetary gears and the rope pulley, where the planetary carrier is driven by the plurality of the planetary gears to rotate coaxially with the sun gear, such that the rope pulley is driven to rotate, and the detection mechanism is driven to move with a rotation of the rope pulley by the rope.

In some embodiments, the rope pulley further defines a guiding groove surrounding the periphery and recessed, and the rope is wound in the guiding groove.

In some embodiments, a transmission ratio of the gear transmission mechanism is greater than 1.

In some embodiments, the detection probe further includes a mounting base, arranged on the housing and surrounded by an inner sidewall of the housing, and defining a mounting hole penetrating the mounting base; where the gear transmission mechanism and the rope transmission mechanism are arranged on a side of the mounting base, and the gear transmission mechanism is connected to the driving mechanism via the mounting hole.

In some embodiments, an opening is defined on an end of the housing close to the detection mechanism and is in communication with the receiving space, and the detection mechanism includes: a transducer, configured to emit a detection signal and receive a feedback signal carrying detection information; a bearing bracket, arranged on the opening of the housing, and including two concave-arc bearing tables; an assembly base, defining an assembly position, where the assembly position is configured to assemble the transducer, is connected to the rope, and includes two cylindrical bosses disposed on two sides of the assembly base, and the two cylindrical bosses are movably supported on the corresponding concave-arc bearing tables respectively, such that the transducer is driven to reciprocatingly oscillate under the action of the rope; and an acoustic window, arranged on a periphery of the transducer, the bearing bracket and the assembly base, arranged on the opening of the housing, and configured to be matched with the transducer to emit the detection signal and receive the feedback signal.

In some embodiments, an assembly groove is defined on each of the two sides of the assembly base, and ends of the rope away from the reversing assembly are respectively arranged in the corresponding assembly grooves.

In some embodiments, the receiving space includes an extension area and a receiving area; and the housing includes: an extension portion, corresponding to the extension area, where the rope transmission mechanism is at least partially accommodated in the extension area; and a handheld portion, connected to an end of the extension portion, and corresponding to the receiving area, where the driving mechanism is accommodated in the receiving area.

According to a second aspect of the embodiments of the present disclosure, a transmission device is provided and applied to a detection probe. The detection probe includes a detection mechanism and a driving mechanism. The transmission device includes: a rope transmission mechanism, including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups.

According to a third aspect of the embodiments of the present disclosure, a detection instrument is provided. The detection instrument includes a host and a detection probe. The detection probe includes: a housing, defining a receiving space; a detection mechanism, disposed on an end of the housing and configured to perform a detection function; a driving mechanism, disposed in the receiving space and configured to output power; a rope transmission mechanism, disposed in the receiving space and including: a rope, connected to the driving mechanism and the detection mechanism respectively, and configured to receive the power output by the driving mechanism, transmit the power to the detection mechanism, and drive the detection mechanism to move; and a reversing assembly, including at least two reversing pulley groups arranged along an extension path of the rope, where the rope sequentially bypasses the two reversing pulley groups, and a transmission direction is changed under an action of the two reversing pulley groups; and a gear transmission mechanism, disposed in the receiving space and connected to the driving mechanism and the rope transmission mechanism respectively, so as to receive the power output by the driving mechanism and transmit the power to the rope transmission mechanism. The host is respectively connected to the detection mechanism and the driving mechanism of the detection probe, such that the driving mechanism is controlled to output the power, and the detection mechanism is controlled to perform the detection function The above-mentioned only present embodiments of the present disclosure, but it should not be construed as a limitation on the scope of the present disclosure. According to the technical solutions and the conception of the present disclosure, all equivalent transformations and modifications made within the scope of the claims of the present disclosure by those skilled in the art shall fall within the scope of coverage of the claims of the present disclosure. In addition, although some specific terms are used in the specification, these terms are only for convenience of explanation and should not be construed as a limitation on the present disclosure.

What is claimed is:

1. A detection probe, comprising:
   a housing, defining a receiving space;
   a detection mechanism, disposed on an end of the housing and configured to perform a detection function;
   a driving mechanism, disposed in the receiving space and configured to output power;
   a rope transmission mechanism, disposed in the receiving space and comprising:
      a rope, connected to the driving mechanism and the detection mechanism respectively, and configured to receive the power output by the driving mechanism, transmit the power to the detection mechanism, and drive the detection mechanism to move; and
      a reversing assembly, comprising at least two reversing pulley groups arranged along an extension path of the rope, wherein the rope sequentially bypasses the two reversing pulley groups, and a transmission direction is changed under an action of the two reversing pulley groups; and
      a tensioning assembly, arranged on the extension path of the rope and configured to apply force to the rope to make the rope in a tensioned state; and
   a gear transmission mechanism, disposed in the receiving space and connected to the driving mechanism and the rope transmission mechanism respectively, so as to receive the power output by the driving mechanism and transmit the power to the rope transmission mechanism;
   wherein the detection probe further comprises a support shaft connected to the housing; and
   the tensioning assembly comprises:
      a tensioning adjustment base, rotatably connected to the support shaft;
      one or more tensioning pulleys, rotatably connected to the tensioning adjustment base, wherein the rope is wound on a periphery of the tensioning pulley, respectively; and
      a force applying member, configured to apply a tensioning adjustment force to the tensioning adjustment base, such that the tensioning adjustment base rotates around the support shaft, and applies force to the rope through the tensioning pulley to make the rope in the tensioned state;
   wherein the detection probe further comprises one of a case I and a case II;
   in the case I, a number of the one or more tensioning pulleys is two; and
   the tensioning adjustment base comprises:
      a first adjusting arm;
      a second adjusting arm, connected to the first adjusting arm, wherein the tensioning adjustment base is rotatably connected to the support shaft at a connection between the first adjusting arm and the second adjusting arm; and
      a first tensioning pulley shaft, connected to an end of the first adjusting arm away from the second adjusting arm, wherein two tensioning pulleys are rotatably sleeved on the first tensioning pulley shaft, respectively;
   wherein the force applying member is connected to an end of the second adjusting arm away from the first adjusting arm, and is configured to apply the tensioning adjustment force to the end of the second adjusting arm away from the first adjusting arm, such that the tensioning adjustment base rotates around the support shaft, the two tensioning pulleys adaptively rotate around the first tensioning pulley shaft and apply force to the rope, and the rope is in the tensioned state;
   in the case II, a number of the one or more tensioning pulleys is two; and
   the tensioning adjustment base comprises:
      a rotating arm, an end of the rotating arm being rotatably connected to the support shaft; and
      a second tensioning pulley shaft, arranged at an end of the rotating arm away from the support shaft, wherein two tensioning pulleys are rotatably sleeved on the second tensioning pulley shaft, respectively:
   wherein the force applying member is connected to the second tensioning pulley shaft and is configured to apply the tensioning adjustment force to the second tensioning pulley shaft, such that the tensioning adjustment base rotates around the support shaft, the two tensioning pulleys adaptively rotate around the second tensioning pulley shaft and apply force to the rope, and the rope is in the tensioned state.

2. The detection probe according to claim 1, wherein in the case II, the detection probe further comprises a support member connected to the housing; and
   the force applying member is a torsional elastic member, and comprises:
      a torsional elastic portion, sleeved around a periphery of the support shaft;
      a first support end, connected to one side of the torsional elastic portion and abutting against the support member; and
      a second support end, connected to the other side of the torsional elastic portion, abutting against the second tensioning pulley shaft, and applying the tensioning adjustment force to the second tensioning pulley shaft under an elastic force of the torsional elastic portion.

3. The detection probe according to claim 1, wherein the rope transmission mechanism further comprises:
   a rope pulley, wherein the rope is wound on a periphery of the rope pulley;
   a stabilizing pulley group, arranged between the rope pulley and the reversing assembly along the extension path of the rope, and comprising two stabilizing pulleys spaced apart from each other, wherein two sides of the rope are respectively wound on peripheries of the corresponding stabilizing pulleys between the two stabilizing pulleys.

4. The detection probe according to claim 1, wherein the rope transmission mechanism further comprises a rope pulley, and the rope is wound on a periphery of the rope pulley; and
   the gear transmission mechanism comprises:
      a sun gear, connected to the driving mechanism and rotating under driving of the driving mechanism;
      a ring gear, sleeved on a periphery of the sun gear, arranged coaxially with the sun gear, and spaced apart from the sun gear;
      a plurality of planetary gears, arranged between the sun gear and the ring gear, and spaced apart from each other, wherein one side of each of the plurality of planetary gears is engaged with the sun gear, and the other side of each of the plurality of planetary gears is engaged with an inner side of the ring gear, such that the plurality of planetary gears rotate with the sun gear; and a planetary carrier, connected to the plurality of planetary gears and the rope pulley, wherein the planetary carrier is driven by the plurality of the planetary gears to rotate coaxially with the sun gear, such that the rope pulley is driven to rotate, and the detection mechanism is driven to move with a rotation of the rope pulley by the rope.

5. The detection probe according to claim 1, wherein a transmission ratio of the gear transmission mechanism is greater than 1.

6. The detection probe according to claim 1, further comprising:
a mounting base, arranged on the housing and surrounded by an inner sidewall of the housing, and defining a mounting hole penetrating the mounting base;
wherein the gear transmission mechanism and the rope transmission mechanism are arranged on a side of the mounting base, and the gear transmission mechanism is connected to the driving mechanism via the mounting hole.

7. The detection probe according to claim 1, wherein the receiving space comprises an extension area and a receiving area; and
the housing comprises:
an extension portion, corresponding to the extension area, wherein the rope transmission mechanism is at least partially accommodated in the extension area; and
a handheld portion, connected to an end of the extension portion, and corresponding to the receiving area, wherein the driving mechanism is accommodated in the receiving area.

8. The detection probe according to claim 1, wherein in the case I, the first adjusting arm and the second adjusting arm are crosswise connected to each other, and the tensioning adjustment base is rotatably sleeved on a periphery of the support shaft at the connection.

9. The detection probe according to claim 1, wherein in the case I, the detection probe further comprises a fixing rod connected to the housing, and the tensioning adjustment base further comprises a connecting rod arranged at the end of the second adjusting arm away from the first adjusting arm;
the force applying member comprises two stretching elastic members, one end of each of the stretching elastic members is connected to the fixing rod, and the other end of each of the stretching elastic members is connected to the connecting rod and configured to apply the tensioning adjustment force to the connecting rod.

10. The detection probe according to claim 9, wherein the detection probe further comprises a first shaft and a second shaft which are connected to the housing and spaced apart from each other, and the first shaft and the second shaft are arranged in parallel with each other; and
the fixing rod is parallel to and spaced apart from the first shaft and the second shaft.

11. The detection probe according to claim 1, wherein the detection probe further comprises a first shaft and a second shaft which are connected to the housing and spaced apart from each other; and the two reversing pulley groups comprise:
two first reversing pulleys, rotatably sleeved on a periphery of the first shaft respectively, and spaced apart from each other; and
two second reversing pulleys, rotatably sleeved on a periphery of the second shaft respectively, and spaced apart from each other;
wherein along the extension path, the rope is sequentially wound on a corresponding periphery of each of the first reversing pulley and the second reversing pulley in a staggered mode, so as to change the transmission direction.

12. The detection probe according to claim 11,
wherein in the case I, the tensioning adjustment base is sleeved on the periphery of the first shaft between the two first reversing pulleys; or
wherein in the case II, the tensioning adjustment base is sleeved on the periphery of the first shaft on two sides of two first reversing pulleys.

13. The detection probe according to claim 11, wherein two ends of the rope are further wound on a corresponding periphery of each of the first reversing pulley, the tensioning pulley and the second reversing pulley in sequence.

14. The detection probe according to claim 1, wherein the rope transmission mechanism further comprises a rope pulley, and the rope is wound on a periphery of the rope pulley; and
the gear transmission mechanism comprises:
a driving shaft, connected to the driving mechanism and rotating under driving of the driving mechanism;
a driving gear, arranged on an end of the driving shaft and rotating synchronously with the driving shaft;
a driven gear, engaged with the driving gear and rotating with the driving gear; and
a driven shaft, connected to the driven gear and the rope pulley respectively, moving synchronously with the driven gear, driving the rope pulley to rotate, and the rope driving the detection mechanism to move with a rotation of the rope pulley.

15. The detection probe according to claim 14, further comprising:
a shaft coupling, an end of the shaft coupling being connected to the driving mechanism, and the other end of the shaft coupling being connected to the driving shaft, so as to transmit the power output by the driving mechanism to the driving shaft.

16. The detection probe according to claim 14, wherein the rope pulley further defines a guiding groove surrounding the periphery of the rope pulley and recessed, and the rope is wound in the guiding groove.

17. The detection probe according to claim 1, wherein an opening is defined on an end of the housing close to the detection mechanism and is in communication with the receiving space, and the detection mechanism comprises:
a transducer, configured to emit a detection signal and receive a feedback signal carrying detection information;
a bearing bracket, arranged on the opening of the housing, and comprising two concave-arc bearing tables;
an assembly base, defining an assembly position, wherein the assembly position is configured to assemble the transducer, is connected to the rope, and comprises two cylindrical bosses disposed on two sides of the assembly base, and the two cylindrical bosses are movably supported on the corresponding concave-arc bearing tables respectively, such that the transducer is driven to reciprocatingly oscillate under the action of the rope; and an acoustic window, arranged on a periphery of the transducer, the bearing bracket and the assembly base, arranged on the opening of the housing, and configured to be matched with the transducer to emit the detection signal and receive the feedback signal.

18. The detection probe according to claim 17, wherein an assembly groove is defined on each of the two sides of the assembly base, and ends of the rope away from the reversing assembly are respectively arranged in the corresponding assembly grooves.

19. A transmission device applied to a detection probe, the detection probe comprising a detection mechanism and a driving mechanism, and the transmission device comprising:
   a rope transmission mechanism, comprising:
      a rope, connected to the driving mechanism and the detection mechanism respectively, and configured to receive the power output by the driving mechanism, transmit the power to the detection mechanism, and drive the detection mechanism to move; and
      a reversing assembly, comprising at least two reversing pulley groups arranged along an extension path of the rope, wherein the rope sequentially bypasses the two reversing pulley groups, and a transmission direction is changed under an action of the two reversing pulley groups; and
   a tensioning assembly, arranged on the extension path of the rope and configured to apply force to the rope to make the rope in a tensioned state;
   wherein the detection probe further comprises a support shaft connected to the housing and a gear transmission mechanism, and the gear transmission mechanism is disposed in the receiving space and connected to the driving mechanism and the rope transmission mechanism respectively, so as to receive the power output by the driving mechanism and transmit the power to the rope transmission mechanism;
   wherein the tensioning assembly comprises:
      a tensioning adjustment base, rotatably connected to the support shaft;
      one or more tensioning pulleys, rotatably connected to the tensioning adjustment base, wherein the rope is wound on a periphery of the tensioning pulley, respectively; and
      a force applying member, configured to apply a tensioning adjustment force to the tensioning adjustment base, such that the tensioning adjustment base rotates around the support shaft, and applies force to the rope through the tensioning pulley to make the rope in the tensioned state;
   wherein the detection probe further comprises one of a case I and a case II;
   in the case I, a number of the one or more tensioning pulleys is two; and
   the tensioning adjustment base comprises:
      a first adjusting arm;
      a second adjusting arm, connected to the first adjusting arm, wherein the tensioning adjustment base is rotatably connected to the support shaft at a connection between the first adjusting arm and the second adjusting arm; and
      a first tensioning pulley shaft, connected to an end of the first adjusting arm away from the second adjusting arm, wherein two tensioning pulleys are rotatably sleeved on the first tensioning pulley shaft, respectively;
   wherein the force applying member is connected to an end of the second adjusting arm away from the first adjusting arm, and is configured to apply the tensioning adjustment force to the end of the second adjusting arm away from the first adjusting arm, such that the tensioning adjustment base rotates around the support shaft, the two tensioning pulleys adaptively rotate around the first tensioning pulley shaft and apply force to the rope, and the rope is in the tensioned state;
   in the case II, a number of the one or more tensioning pulleys is two; and
   the tensioning adjustment base comprises:
      a rotating arm, an end of the rotating arm being rotatably connected to the support shaft; and
      a second tensioning pulley shaft, arranged at an end of the rotating arm away from the support shaft, wherein two tensioning pulleys are rotatably sleeved on the second tensioning pulley shaft, respectively;
   wherein the force applying member is connected to the second tensioning pulley shaft and is configured to apply the tensioning adjustment force to the second tensioning pulley shaft, such that the tensioning adjustment base rotates around the support shaft, the two tensioning pulleys adaptively rotate around the second tensioning pulley shaft and apply force to the rope, and the rope is in the tensioned state.

20. A detection instrument, comprising: a host and a detection probe;
   wherein the detection probe comprises:
      a housing, defining a receiving space;
      a detection mechanism, disposed on an end of the housing and configured to perform a detection function;
      a driving mechanism, disposed in the receiving space and configured to output power;
      a rope transmission mechanism, disposed in the receiving space and comprising:
         a rope, connected to the driving mechanism and the detection mechanism respectively, and configured to receive the power output by the driving mechanism, transmit the power to the detection mechanism, and drive the detection mechanism to move; and
         a reversing assembly, comprising at least two reversing pulley groups arranged along an extension path of the rope, wherein the rope sequentially bypasses the two reversing pulley groups, and a transmission direction is changed under an action of the two reversing pulley groups; and
      a tensioning assembly, arranged on the extension path of the rope and configured to apply force to the rope to make the rope in a tensioned state; and
      a gear transmission mechanism, disposed in the receiving space and connected to the driving mechanism and the rope transmission mechanism respectively, so as to receive the power output by the driving mechanism and transmit the power to the rope transmission mechanism;
   wherein the detection probe further comprises a support shaft connected to the housing; and
   the tensioning assembly comprises:
      a tensioning adjustment base, rotatably connected to the support shaft;

one or more tensioning pulleys, rotatably connected to the tensioning adjustment base, wherein the rope is wound on a periphery of the tensioning pulley, respectively; and a force applying member, configured to apply a tensioning adjustment force to the tensioning adjustment base, such that the tensioning adjustment base rotates around the support shaft, and applies force to the rope through the tensioning pulley to make the rope in the tensioned state;

wherein the detection probe further comprises one of a case I and a case II;

in the case I, a number of the one or more tensioning pulleys is two; and the tensioning adjustment base comprises:
　a first adjusting arm;
　a second adjusting arm, connected to the first adjusting arm, wherein the tensioning adjustment base is rotatably connected to the support shaft at a connection between the first adjusting arm and the second adjusting arm; and
　a first tensioning pulley shaft, connected to an end of the first adjusting arm away from the second adjusting arm, wherein two tensioning pulleys are rotatably sleeved on the first tensioning pulley shaft, respectively;

wherein the force applying member is connected to an end of the second adjusting arm away from the first adjusting arm, and is configured to apply the tensioning adjustment force to the end of the second adjusting arm away from the first adjusting arm, such that the tensioning adjustment base rotates around the support shaft, the two tensioning pulleys adaptively rotate around the first tensioning pulley shaft and apply force to the rope, and the rope is in the tensioned state;

in the case II, a number of the one or more tensioning pulleys is two; and the tensioning adjustment base comprises:
　a rotating arm, an end of the rotating arm being rotatably connected to the support shaft; and
　a second tensioning pulley shaft, arranged at an end of the rotating arm away from the support shaft, wherein two tensioning pulleys are rotatably sleeved on the second tensioning pulley shaft, respectively;

wherein the force applying member is connected to the second tensioning pulley shaft and is configured to apply the tensioning adjustment force to the second tensioning pulley shaft, such that the tensioning adjustment base rotates around the support shaft, the two tensioning pulleys adaptively rotate around the second tensioning pulley shaft and apply force to the rope, and the rope is in the tensioned state;

wherein the host is respectively connected to the detection mechanism and the driving mechanism of the detection probe, such that the driving mechanism is controlled to output the power, and the detection mechanism is controlled to perform the detection function.

\* \* \* \* \*